United States Patent
Schinzel

(10) Patent No.: US 6,458,324 B1
(45) Date of Patent: Oct. 1, 2002

(54) RECEIVING DEVICE AND RECEIVING MEANS, TRANSFER DEVICE, AND WORKSTATION AND METHOD FOR THEIR OPERATION

(75) Inventor: Fred Schinzel, Männedorf (CH)

(73) Assignee: Tecan Trading AG, Männedorf (CH)

(*) Notice: Subject to any disclaimer, the term of this patent is extended or adjusted under 35 U.S.C. 154(b) by 0 days.

(21) Appl. No.: 09/438,871

(22) Filed: Nov. 12, 1999

(30) Foreign Application Priority Data

Nov. 17, 1998 (CH) ............................................. 2 297/98

(51) Int. Cl.⁷ ............................. G01N 35/02; B25J 15/00
(52) U.S. Cl. ............................ 422/65; 422/63; 422/72; 422/102; 422/104; 436/43; 436/45; 436/47; 436/48; 414/749.1; 414/751.1; 494/16; 901/31; 901/41
(58) Field of Search ............................ 422/63, 65, 72, 422/102, 104; 436/43, 45, 47–48; 414/749.1, 751.1; 494/16; 901/31, 41

(56) References Cited

U.S. PATENT DOCUMENTS

| 4,660,274 A | * | 4/1987 | Goumas et al. ............... 29/568 |
| 4,735,776 A | * | 4/1988 | Yamamoto et al. ............ 422/65 |
| 4,835,707 A | * | 5/1989 | Amano et al. ............... 364/497 |
| 5,479,969 A | * | 1/1996 | Hardie et al. ................ 141/130 |
| 5,544,683 A | * | 8/1996 | Guhl ............................. 141/65 |
| 5,681,530 A | * | 10/1997 | Kuster et al. .................. 422/63 |
| 5,769,775 A | * | 6/1998 | Quinlan et al. ................ 494/10 |
| 6,060,022 A | * | 5/2000 | Pang et al. .................... 422/65 |
| 6,264,419 B1 | * | 7/2001 | Schinzel .................. 414/751.1 |

FOREIGN PATENT DOCUMENTS

JP         6213564 A    *   8/1994

* cited by examiner

Primary Examiner—Jeffrey Snay
Assistant Examiner—Kathryn Bex
(74) Attorney, Agent, or Firm—Notaro & Michalos P.C.

(57) ABSTRACT

A workstation has a transfer device with a gripper which is suitable for gripping sample tubes by a gripper clamp and for moving them from a sample tube rack to a sample tube bucket, for example for centrifuging. The transfer device has a receiving device (23) which can be gripped on a cylindrical upper handling part (25) by the gripper and removed from a holder (24) in which it has been placed in a defined position. It has an intermediate part (33) with, on its lower end, four hooks (37) which are arranged at the apices of a rectangle and can engage eyes in the sample tube buckets. After use, the receiving device (23) is replaced in the holder (24).

14 Claims, 3 Drawing Sheets

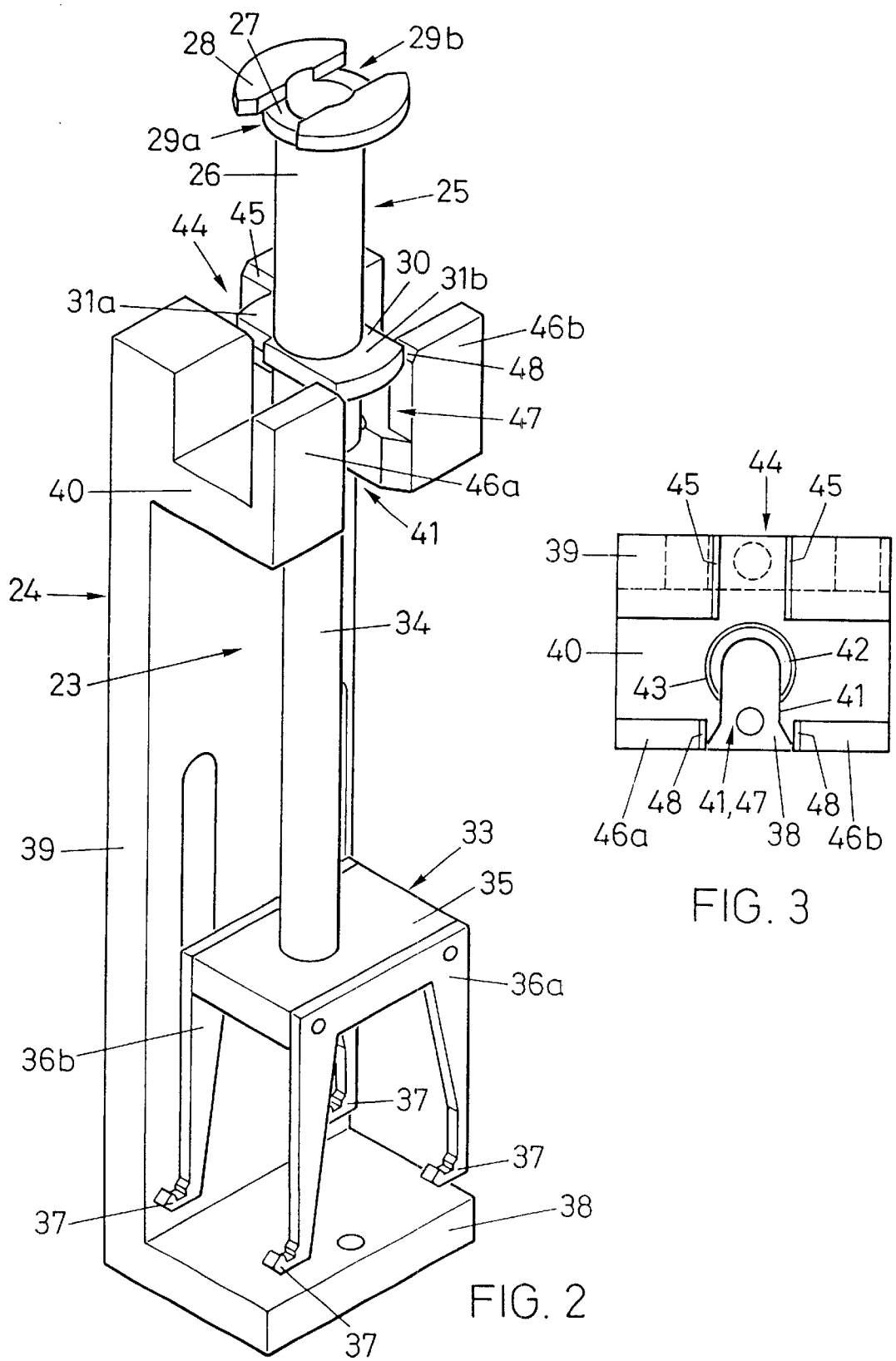

RECEIVING DEVICE AND RECEIVING MEANS, TRANSFER DEVICE, AND WORKSTATION AND METHOD FOR THEIR OPERATION

FIELD OF THE INVENTION

The invention relates to a receiving device for picking up objects by means of a gripper, a receiving means and transfer means each comprising such a receiving device, and a workstation and method for their operation. Devices and methods of this type are used in chemical, biological and medical laboratories for handling samples, in particular for preparing for centrifuging said samples.

PRIOR ART

WO-A-98/01 760 discloses a gripper having a gripper clamp which is suitable for gripping sample tubes. By means of the gripper, individual sample tubes can therefore be moved from a sample tube rack to a sample tube bucket, which is then introduced into a centrifuge. To enable this too to be effected by means of the gripper, the sample tube buckets must be provided with a cylindrical handle, i.e. must be specially designed.

WO-A-90/08 326 discloses a workstation comprising a gripper which is suitable for gripping entire rotors which are suitable for use in centrifuges and are loaded and unloaded by means of a separate processing unit outside the centrifuge, and for inserting said rotors into said centrifuge and for removing them from said centrifuge. The use of sample tube buckets is not envisaged. The design of the workstation is relatively complicated.

SUMMARY OF THE INVENTION

It is the object of the invention to provide a receiving device which makes it possible, by means of a gripper which is suitable for directly gripping sample tubes, also to pick up and to move other objects, in particular sample tube buckets, without these having to be specially adapted to the gripper. It is also intended to provide a receiving means which furthermore comprises a holding device in which the receiving device can be placed so that it can be easily and securely approached and gripped by the gripper.

It is also intended to provide a transfer device for picking up, moving and setting down individual sample tubes, which transfer device can pick up and move both individual sample tubes and other objects, in particular customary sample tube buckets, by means of a single gripper. Finally, it is intended to provide a workstation in which in particular the feeding, distribution and centrifuging of sample tubes is substantially facilitated, and a method for its operation which is suitable for this purpose.

These objects are achieved by the invention as characterized in the claims. A gripper suitable for gripping and moving sample tubes is supplemented by the receiving device or receiving means according to the invention to give a transfer device according to the invention, which device, inter alia, also permits rapid loading of a centrifuge by relatively economical means since it can also handle sample tube buckets. After the distribution of the sample tubes over the sample tube buckets, the latter can therefore also be introduced into the centrifuge by means of the same transfer device, permitting significant savings.

The workstation according to the invention combines the features of a plurality of components according to the invention to give a configuration particularly suitable for rapidly carrying out the centrifuging step, in particular by the method according to the invention, and is furthermore relatively economical. It can also be suitably designed for carrying out further processing steps.

BRIEF DESCRIPTION OF THE DRAWINGS

The invention is explained in more detail below with reference to Figures which represent only one embodiment.

FIG. 2 shows a perspective view of the receiving means according to the invention, FIG. 3 shows a plan view of a part of the receiving means according to the invention, shown in FIG. 2.

DESCRIPTION OF THE PREFERRED EMBODIMENTS

Figure 1:
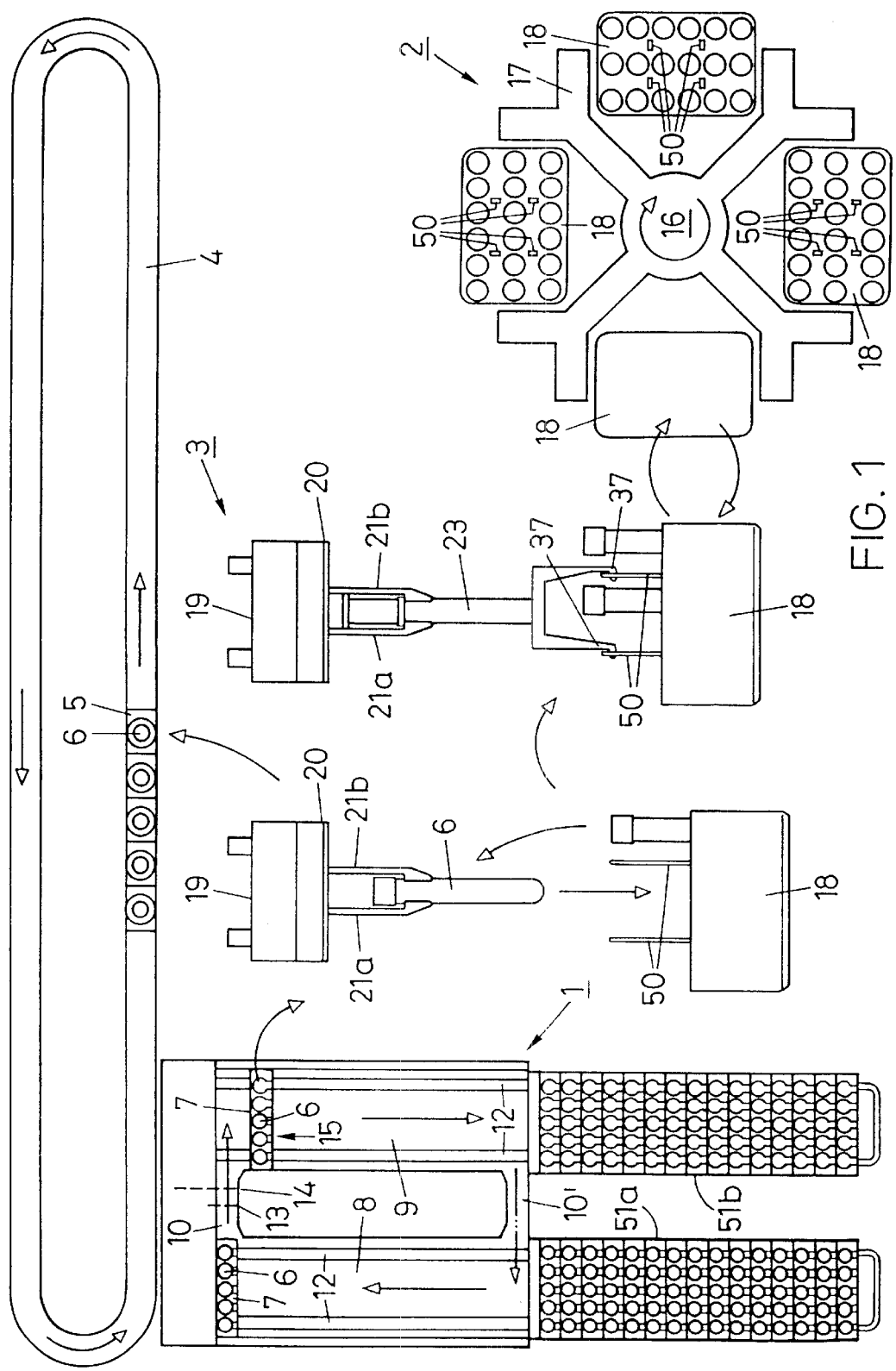
FIG. 1 shows a schematic overview of a workstation according to the invention and the sequence of the method according to the invention.

FIG. 1 shows a workstation comprising a feed device 1, a centrifuge 2 and a transfer device 3. Also present is a conveying device 4 which brings individual sample tubes 6 inserted in carriers 5 to other processing modules (not shown).

The feed device 1 is used for feeding sample tubes 6 which are delivered, usually in the form of several sample tubes but under certain circumstances also individually, in sample tube racks 7 to the workstation and also for checking and classifying them. It comprises a feed track 8 and a return track 9 which is arranged a small distance away from said feed track and parallel to it, both of which are equipped with conveyor belts 12. The end of the feed track 8 is connected to the beginning of the return track 9 by a transverse intermediate track 10. On the opposite side, a height scanner 13 having two reflecting cells arranged at different heights and a bar code reader 14 are arranged side by side on the intermediate track 10. Moreover, a second transverse intermediate track 10 which connects the end of the return track 9 to the beginning of the feed track 8 can be provided. A balance 15 by means of which the weight of the sample tube rack 7 present in each case on it can be determined is installed at the beginning of the return track 9.

The centrifuge 2 has a cross 17 which is rotatable about a central axis 16 of rotation and between whose arms four sample tube buckets 18 can be suspended, which buckets are completely or partly filled with sample tubes. The sample tubes are inserted into recesses which are arranged in a plurality of parallel rows in the respective sample tube bucket. The sample tube buckets 18 form two pairs, those belonging to a pair being diametrically opposite one another with respect to the axis 16 of rotation. The weights of the sample tube buckets 18 of a pair may differ from one another by not more than a specific maximum value, which is usually between 15 g and 20 g, in order to limit the imbalance.

The transfer device 3 comprises a gripper 19 (shown in two different positions in FIG. 1) which is suspended in such a way that it can travel in a controlled manner in three directions, in particular in two horizontal directions normal to one another and perpendicularly. It has a downward-projecting gripper clamp 20 which is rotatable about a perpendicular axis in a controlled manner and comprises two gripper fingers 21a,b which are opposite one another and can be moved away from one another or towards one another for, respectively, opening and closing the gripper clamp 20. The gripper fingers 21a,b have, on their end regions, grooved contact surfaces 22 (FIG. 5) which face one another and are covered with a nonslip, resilient coating, for example of polyurethane, for improving the adhesion. The gripper clamp 20 is thus directly suitable for gripping and holding sample tubes 6 and objects of similar shape.

Figure 5:
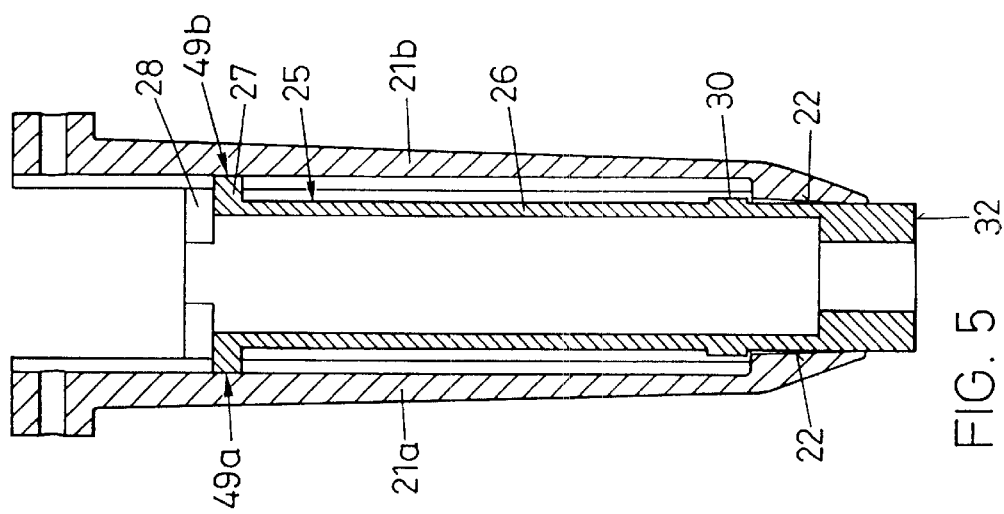
FIG. 4 shows a perspective view of parts of the transfer device according to the invention and FIG. 5 shows a vertical longitudinal section through those parts of the transfer device according to the invention which are shown in FIG. 4.
Figure 4:
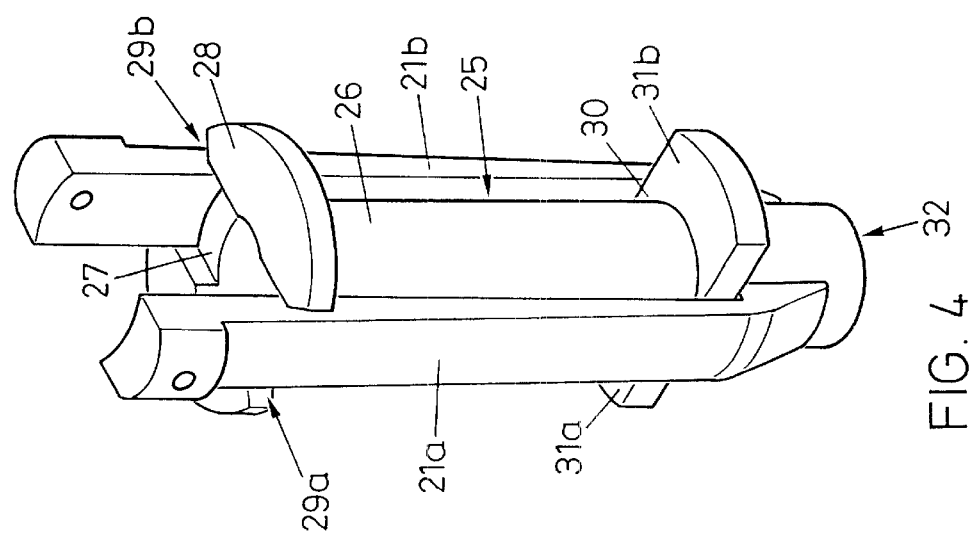

To enable other objects too, such as, for example, sample tube buckets 18, to be gripped by the gripper 19, a receiving means (FIG. 2) which comprises a receiving device 23 is arranged in the access region of said gripper, as well as a holder 24 in which said receiving device is deposited. The receiving device 23 has an upper handling part 25 which comprises a basic member 26 which is cylindrical, i.e. corresponds in its shape essentially to a sample tube, and carries an all-round first collar 27 at its upper end. Mounted directly above this is a larger second collar 28 which has two recesses 29a,b opposite one another. In the vicinity of its lower end, the basic member 26 carries an elongated third collar 30 which forms two longer extensions 31a,b opposite one another but is only narrow below the recesses 29a,b. The lower end of the basic member 26 forms a downward-pointing annular stop surface 32 (FIGS. 4, 5).

Adjacent (FIG. 2) to the bottom of the basic member 26 of the handling part 25 is an intermediate part 33 which is connected, for example screwed, to it and has a cylindrical shaft 34 and a support plate 35 which is fastened to its lower end and to the longitudinal sides of which are screwed two U-shaped parts 36a,b, each of which forms two downward-projecting hooks 37 in such a way that the positions of the four identically oriented hooks 37 form the apices of a horizontal rectangle.

The holder 24 has a bottom plate 38 to which is fastened a perpendicular rear wall 39 which carries, slightly below its upper end, a horizontal retaining plate 40 located above the bottom plate 38. Said retaining plate has, at its edge facing away from the rear wall 39, a slot 41 which terminates in a semicircle and is surrounded, on the upper side of the retaining plate 40, by a support strip 42 (FIG. 3) which forms a ring segment. It is located lower than the surrounding part of the upper side of the retaining plate 40 and is connected to said part via a centring strip 43 inclined inwards in the manner of a funnel. The rear wall 39 is provided with a perpendicular slot 44 which is open at the top, continues through to the retaining plate 40 and has, on its upper edges, bevels 45 sloping downwards in an inward direction. At the front edge, the retaining plate 40 carries two upward-pointing front plates 46a,b which are flush with the rear wall 39 and laterally bound a slightly broader perpendicular slot 47 which is open at the top and likewise has, on its upper edges, bevels 48 sloping downwards in an inward direction.

When the receiving device 23 is placed in the holder 24, the slot 41 receives the shaft 34 of the intermediate part 33 while the stop surface 32 on the lower end of the handling part 25, tightly surrounded by the centring strip 43, rests on the support strip 42. The extensions 31a,b project with little lateral play into the slots 44 and 47, respectively. The three-dimensional position of the receiving device 23 is thus exactly defined, including its rotational position.

If the handling part 25 is held by the gripper clamp 20, the grooved contact surfaces 22 of the gripper fingers 21a,b rest (FIGS. 4, 5), slightly below the third collar 30, against sections of the outside of the cylindrical basic member 26 which form approximately correspondingly convex opposite contact surfaces. The contact surfaces 22 are displaced slightly inwards. The indentations are just below the collar 30 and prevent the handling part 25 from slipping out downwards. The gripper fingers 21a,b are present in the recesses 29a,b in the second collar 28 and form therewith a means for preventing rotation of the handling part 25 about a perpendicular axis as well as for preventing transverse displacement. At the same time, the gripper fingers 21a,b rest with contact regions 49a,b against the outer edge of the first collar 27. Those sections of the gripper fingers 21a,b which are present below the contact area are bent slightly elastically outwards so that the contact surfaces 22 rest against the opposite contact surfaces with a certain contact pressure and fix the basic member 26 immovably there. As a result of the contact of the handling part 25 at two regions a vertical distance apart, said part is also reliably secured to prevent rotations about horizontal axes. The receiving device 23 can thus always be held by the gripper 19 in a defined position and securely guided.

To enable (FIG. 1) the sample tube buckets 18 to be coupled to the receiving device 23, they are provided with four upward-pointing tongues 50 which, in their upper ends, form eyes whose relative position corresponds to that of the hooks 37. The hooks 37 can thus also be introduced into the four eyes for coupling the sample tube bucket 18, whereupon the sample tube bucket 18 can be raised and moved. After said bucket has been set down in t he desired place, the hooks 37 can be removed from the eyes.

If it is intended to process a number of samples in the installation according to FIG. 1, in particular if at least some of them are to be centrifuged, a drawer with sample tube racks 7, each of which is completely or partly filled with sample tubes 6, is delivered and is coupled as drawer 51a to the entrance of the feed track 8. The sample tubes 6 each contain samples to be treated and are provided with bar code labels which identify said samples. The sample tube racks 7 are then moved manually onto the feed track 8, picked up there by the conveyor belts 12 and transported further transversely to their longitudinal direction until the feed track 8 has been filled. One sample tube rack 7 after the other is then pushed transversely to the previous transport direction in the longitudinal direction via the intermediate track 10, the sample tubes 6 being assigned one after the other to one of three different classes by the height scanner 13 with respect to their height. Immediately thereafter, the labels of the sample tubes 6 are read by the bar code reader 14 and the samples are further classified with regard to their subsequent processing; inter alia, it is possible on the basis of the bar code to determine whether a sample is to be centrifuged or not.

When the sample tube rack 7 reaches the beginning of the return track 9, it enters the range of action of the conveyor belts 12 of said track, which further transport it, now in a direction opposite to the transport direction of the feed track 8 and once again transversely to its longitudinal direction, until it is present above the balance 15, which is then activated. Said balance is raised until the sample tube rack 7 rests on the balance 15 and is slightly raised from the conveyor belts 12 by said balance. The total weight of the sample tube rack 7 is then determined. A first sample tube 6 is then gripped by means of the gripper 19, raised and removed from the sample tube rack 7. The weight of the sample tube rack 7 is then again determined.

If the weight of the removed sample tube 6 is required, which is the case particularly when the sample present in said tube is to be centrifuged, it is determined as the difference between the weights of the sample tube rack 7 determined before and after removal of said tube from the sample tube rack 7. According to the result of the weight determination, the sample tube 6 can then be deposited in one of four sample tube buckets 18 which are present in the access region of the gripper 19. As already explained, a weight distribution is strived for in which the maximum permissible imbalances for the centrifuge 2 are not exceeded. In addition to the weight of the sample tube 6 removed, it is of course also possible to take into account other parameters for the assignment, for example optionally the total weight of the sample tubes 6 remaining in the sample tube rack 7, which can be determined from the last weighing and the known empty weight thereof, or the determined heights of the sample tubes 6. If the sample is not to be centrifuged, the sample tube 6 can be placed directly on one of the carriers 5 of the conveying device 4, with or without determination of the weight of said sample tube.

When further sample tubes 6 are removed, the procedure is exactly the same as that described above. After each removal, the total weight of the sample tube rack 7 is determined and the weight of the sample tube just removed is determined from the difference from the result of the preceding weighing. Once all sample tubes which are to be removed have been removed—usually these are all tubes but it is possible that individual sample tubes are not to be removed, for example if the bar code was not legible—the balance 15 is lowered again to its inactive position and the sample tube rack 7 is further transported, the next one usually simultaneously being moved into the region of the balance 15. At the latest when the return track 9 has been completely filled with—usually empty—sample tube racks 7, the drawer 51*b* is coupled to the exit of said track, which triggers both lowering of a stop at the end of the return track 9, which previously prevented sample tube racks from being pushed beyond the end of said track, and starting of the conveyor belts 12 thereof, which move all sample tube racks 7 from the return track 9 onto the drawer 51*b*, where, owing to the inclination thereof, they slip outwards until they stop. When it is full, the drawer 51*b* is uncoupled and removed. The feed device 1 can optionally also be operated so that the sample tube racks are moved from the end of the return track 9 via the second intermediate track 10 back to the beginning of the feed track 8 and thus revolve in a closed circle. In this case, they are manually loaded with sample tubes.

Once the sample tube buckets 18 have been filled, they must be introduced into the centrifuge 2. For this purpose, the gripper 19 approaches the holder 24 (FIG. 2) where the gripper clamp 20 grips the handling part 25, raises it and pulls out the receiving device 23 in a forward direction. Thereafter, a first sample tube bucket 18 in the centrifuge 2 is gripped by a procedure in which the receiving device 23 is positioned by means of the gripper 19 so that the hooks 37 are present in front of the eyes in the tongues 50, whereupon the hooks 37 are introduced into the eyes by a horizontal displacement. The gripper 19 is then raised so that the hooks 37 securely engage the eyes. The sample tube bucket 18 coupled in this manner can now be raised out of the centrifuge 2 and moved to a suitable place. Thereafter, the receiving device 23 is disconnected from the sample tube bucket 18 by a movement sequence opposite to that described above. In a corresponding manner, one of the newly filled sample tube buckets 18 is then moved to the centrifuge 2 and introduced into said centrifuge. Finally, all four sample tube buckets 18 in the centrifuge 2 are thus replaced, the axis 16 of rotation performing in each case a quarter of a rotation before the replacement of a further sample tube bucket 18, so that the removal and introduction of the sample tube buckets into the centrifuge 2 always takes place at the same point.

The gripper 19 then again approaches the holder 24 and deposits the receiving device 23 there. The centring strip 43 and the bevels 45 and 48 ensure that, even when deposition is not very precise, the receiving device 23 exactly assumes its defined position where it can be picked up again securely and without difficulties.

The gripper 19 again immediately removes, by means of the gripper clamp 20, a sample tube 6 from one of the sample tube buckets 18 removed from the centrifuge 2 and places it, for example, on one of the carriers 5 of the conveying device 4. From there, it is then moved to the sample tube rack 7 which is present on the balance 15 and removes from said sample tube rack a sample tube 6 which it then brings, in the manner already described further above, to a sample tube bucket 18 and deposits it there. This process is repeated until all sample tubes 6 in the sample tube buckets 18 have been replaced. At the same time, the samples introduced last into the centrifuge 2 are centrifuged.

The method described and the workstation described can be modified in many details without departing from the scope of the invention. Thus, for example, the transfer device may have a plurality of different receiving devices in a plurality of holders, which are suitable for coupling objects of different categories. The workstations may have different modules for distribution, for pipetting and for carrying out other processing steps, all of which are connected to one another by the conveying device and transfer device—of which there may also be a plurality.

LIST OF REFERENCE SYMBOLS

1 Feed device
2 Centrifuge
3 Transfer device
4 Conveying device
5 Carrier
6 Sample tube
7 Sample tube rack
8 Feed track
9 Return track
10, 10' Intermediate tracks
11 Baseplate
12 Conveyor belts
13 Height scanner
14 Bar code reader
15 Balance
16 Axis of rotation
17 Arms
18 Sample tube bucket
19 Gripper
20 Gripper clamp
21*a,b* Gripper fingers
22 Contact surfaces
23 Receiving device
24 Holder
25 Handling part
26 Basic member
26 First collar
28 Second collar
29*a,b* Recesses
30 Third collar
31*a,b* Extensions
32 Stop surface
33 Intermediate part 34 Shaft
35 Support plate
36a,b U-shaped parts
37 Hooks
38 Bottom plate
39 Rear wall
40 Retaining plate
41 Slot
42 Support strip
43 Centring strip
44 Slot
45 Belts
46a,b Front plates
47 Slot
48 Bevels
49a,b Contact regions
50 Tongues
51a,b Drawers

What is claimed is:

1. A receiving device (23) for picking up, moving, and setting down an object (18) with a gripper (19), the receiving device (23) comprising a handling part (25) with a basic member (26) and opposite contact surfaces to be gripped and held by the gripper (19), the receiving device (23) further comprising an intermediate part (33) connected to a lower end of the handling part (25), for coupling to the object (18), the gripper (19) having a gripper clamp (20) with at least two gripper fingers (21a,21b) movable relative to one another for opening and closing, the gripper fingers (21a,21b) having, in end regions thereof, contact surfaces (22) which face one another and, when holding the handling part (25), cooperate with corresponding the opposite contact surfaces on the handling part (25), the handling part (25) further comprising a first (27) collar, a second (28) collar and a third (30) collar, the first and second collars being substantially of cylindrical shape and situated at an upper end of the basic member (26), the second collar (28) comprising recesses (29a,29b) opposite one another for receiving the gripper fingers (21a,21b), the handling part (25) further being substantially cylindrical and having lateral extensions (31a,31b) which form the third collar (30), and wherein the gripper fingers (21a,21b), when holding the handling part (25), rest with contact regions (49a,49b) which are a distance above the contact surfaces (22), against a outer edge of the first collar (27), and wherein the gripper fingers (21a,21b) rest with their contact surfaces (22) against opposite contact surfaces below the third collar (30) of the handling part (25).

2. The receiving device of claim 1, wherein the first and second collars are substantially concentrically arranged, the basic member (26) having substantially the same dimension as sample tubes to be gripped by the gripper fingers that project downwardly.

3. The receiving device of claim 1, wherein the gripper fingers are elastically bent outwardly below the contact regions (49a, 49b).

4. The receiving device of claim 1, wherein the intermediate part (33) has, on a lower end thereof, at least one hook (37) for engaging an object to be picked up.

5. The receiving device of claim 1, wherein the intermediate part (33) has, on a lower end thereof, four hooks (37) for engaging an object to be picked up.

6. The receiving device of claim 1, including a holder (24) in which the receiving device (23) is set down and picked up by the gripper (19) in a defined position.

7. The receiving device of claim 6, wherein the handling part (25) has a downwardly pointing stop surface (32) and the holder (24) has a horizontal retaining plate (40) on which the stop surface (32) rests, with a lateral slot (41) for introducing the receiving device (23).

8. The receiving device of claim 7, wherein the stop surface (32) rests on a lower support strip (42) which partly surrounds an edge of the slot (41) at the upper side of the retaining plate (40) and which is bounded on the outside by a centering strip (43) which is inclined inwardly and closely surrounds the edge of the stop surface (32).

9. The receiving device of claim 7, wherein the handling part (25) has a lateral extension (31a, 31b) and the holder (24) has a slot (44, 47) which, to prevent rotation, closely receives the extension (31a, 31b).

10. A transfer device comprising: a gripper (19) comprising a gripper clamp (20) with at least two downwards projecting gripper fingers (21a, 21b) movable relative to one another for opening and closing, the transfer device including a receiving device (23) for picking up, moving, and setting down an object (18) with the gripper (19), the receiving device (23) comprising a handling part (25) with a basic member (26) and opposite contact surfaces to be gripped and held by the gripper (19), the receiving device (23) further comprising an intermediate part (33) connected to a lower end of the handling part (25), for coupling to the object (18), the gripper fingers (21a,21b) having, in end regions thereof, contact surfaces (22) which face one another and, when holding the handling part (25), cooperate with corresponding the opposite contact surfaces on the handling part (25), the handling part (25) further comprising a first (27) collar, a second (28) collar and a third (30) collar, the first and second collars being substantially of cylindrical shape and situated at an upper end of the basic member (26), the second collar (28) comprising recesses (29a,29b) opposite one another for receiving the gripper fingers (21a,21b), the handling part (25) further being substantially cylindrical and having lateral extensions (31a,31b) which form the third collar (30), and wherein the gripper fingers (21a,21b), when holding the handling part (25), rest with contact regions (49a,49b) which are a distance above the contact surfaces (22), against a outer edge of the first collar (27), and wherein the gripper fingers (21a,21b) rest with their contact surfaces (22) against opposite contact surfaces below the third collar (30) of the handling part (25).

11. Transfer device according to claim 10, wherein the contact surfaces (21) are provided with a nonslip covering.

12. Transfer device according to claim 10, wherein the gripper fingers (21a,21b), when holding the handling part (25), rest with contact regions (49a, 49b), which are a distance above the contact surfaces (22), against the handling part (25), said gripper fingers being elastically bent slightly outwards below said contact regions (49a, 49b).

13. A workstation comprising: a centrifuge (22) and a plurality of sample tube buckets (18), the workstation comprising a transfer device (3) comprising a gripper (19) comprising a gripper clamp (20) with at least two downwards projecting gripper fingers (21a, 21b) movable relative to one another for opening and closing, the transfer device including a receiving device (23) for picking up, moving, and setting down an object (18) with the gripper (19), the receiving device (23) comprising a handling part (25) with a basic member (26) and opposite contact surfaces to be gripped and held by the gripper (19), the receiving device (23) further comprising an intermediate part (33) connected to a lower end of the handling part (25), for coupling to the object (18), the gripper fingers (21a,21b) having, in end regions thereof, contact surfaces (22) which face one another and, when holding the handling part (25), cooperate with corresponding the opposite contact surfaces on the handling part (25), the handling part (25) further comprising a first (27) collar, a second (28) collar and a third (30) collar, the first and second collars being substantially of cylindrical shape and situated at an upper end of the basic member (26), the second collar (28) comprising recesses (29a,29b) opposite one another for receiving the gripper fingers (21a,21b), the handling part (25) further being substantially cylindrical and having lateral extensions (31a,31b) which form the third collar (30), and wherein the gripper fingers (21a,21b), when holding the handling part (25), rest with contact regions (49a,49b) which are a distance above the contact surfaces (22), against a outer edge of the first collar (27), and wherein the gripper fingers (21a,21b) rest with their contact surfaces (22) against opposite contact surfaces below the third collar (30) of the handling part (25), the transfer device removing sample tubes (6) from a sample tube rack (7), for distributing the sample tubes over the sample tube buckets (18), and for introducing the buckets into the centrifuge (2) with the aid of the receiving device (23).

14. The workstation of claim 13, wherein the sample tube buckets (18) each have at least one eye, in particular a plurality of eyes a horizontal distance apart, and the intermediate part (33) is provided with correspondingly arranged hooks (37) for engaging the at least one eye.

* * * * *